United States Patent
McMinn

(10) Patent No.: US 7,815,684 B2
(45) Date of Patent: Oct. 19, 2010

(54) KNEE PROSTHESIS

(76) Inventor: Derek James Wallace McMinn, Calcot Farm, Calcot Hill, Clent, Stourbridge, West Midlands (GB) DY9 9RX ( * ) Notice: Subject to any disclaimer, the term of this patent is extended or adjusted under 35 U.S.C. 154(b) by 192 days.

(21) Appl. No.: 11/351,529

(22) Filed: Feb. 10, 2006

(65) Prior Publication Data
US 2006/0265080 A1    Nov. 23, 2006

(30) Foreign Application Priority Data
May 19, 2005    (GB) ................... 0510193.6

(51) Int. Cl.
*A61F 2/38* (2006.01)

(52) U.S. Cl. .............. 623/20.27; 623/20.14; 623/20.21; 623/20.24; 623/20.28

(58) Field of Classification Search ............. 623/20.21, 623/20.26–20.29, 20.31, 20.33, 20.14
See application file for complete search history.

(56) References Cited

U.S. PATENT DOCUMENTS

| | | | | |
|---|---|---|---|---|
| 4,298,992 A | | 11/1981 | Burstein et al. .............. 3/1.911 |
| 5,011,496 A | * | 4/1991 | Forte et al. ............... 623/20.27 |
| 5,116,375 A | | 5/1992 | Hofmann | |
| 5,370,699 A | * | 12/1994 | Hood et al. .............. 623/20.28 |
| 5,387,240 A | | 2/1995 | Pottenger et al. .............. 623/20 |
| 5,658,342 A | | 8/1997 | Draganich et al. ............. 623/20 |
| 5,824,100 A | | 10/1998 | Kester et al. | |
| 6,123,729 A | | 9/2000 | Insall et al. ............... 623/20.31 |
| 6,413,279 B1 | | 7/2002 | Metzger et al. | |
| 2004/0243244 A1 | * | 12/2004 | Otto et al. ................. 623/20.27 |
| 2005/0143832 A1 | * | 6/2005 | Carson .................... 623/20.28 |
| 2005/0209701 A1 | * | 9/2005 | Suguro et al. ............ 623/20.27 |
| 2006/0265078 A1 | | 11/2006 | McMinn | |

FOREIGN PATENT DOCUMENTS

| | | |
|---|---|---|
| EP | WO2004069104 A1 | 8/2004 |
| GB | 2351236 A | 12/2000 |
| WO | 00/23011 A1 | 4/2000 |

OTHER PUBLICATIONS

Corresponding United Kingdom Search Report.

* cited by examiner

*Primary Examiner*—Alvin J Stewart
*Assistant Examiner*—Yashita Sharma
(74) *Attorney, Agent, or Firm*—Fulbright & Jaworski LLP

(57) ABSTRACT

A knee prosthesis comprises a femoral component, a tibial component and a bearing component between the femoral and tibial components. The femoral component defines medial and lateral condyles and an intercondylar box, and the bearing component has respective surfaces matching the condylar surfaces and engaging therewith when the knee is extended over a first range of flexion. The femoral component defines at the area of the intercondylar box a cam and a follower is defined by the bearing component, the cam and following engaging over a second range of flexion.

10 Claims, 3 Drawing Sheets

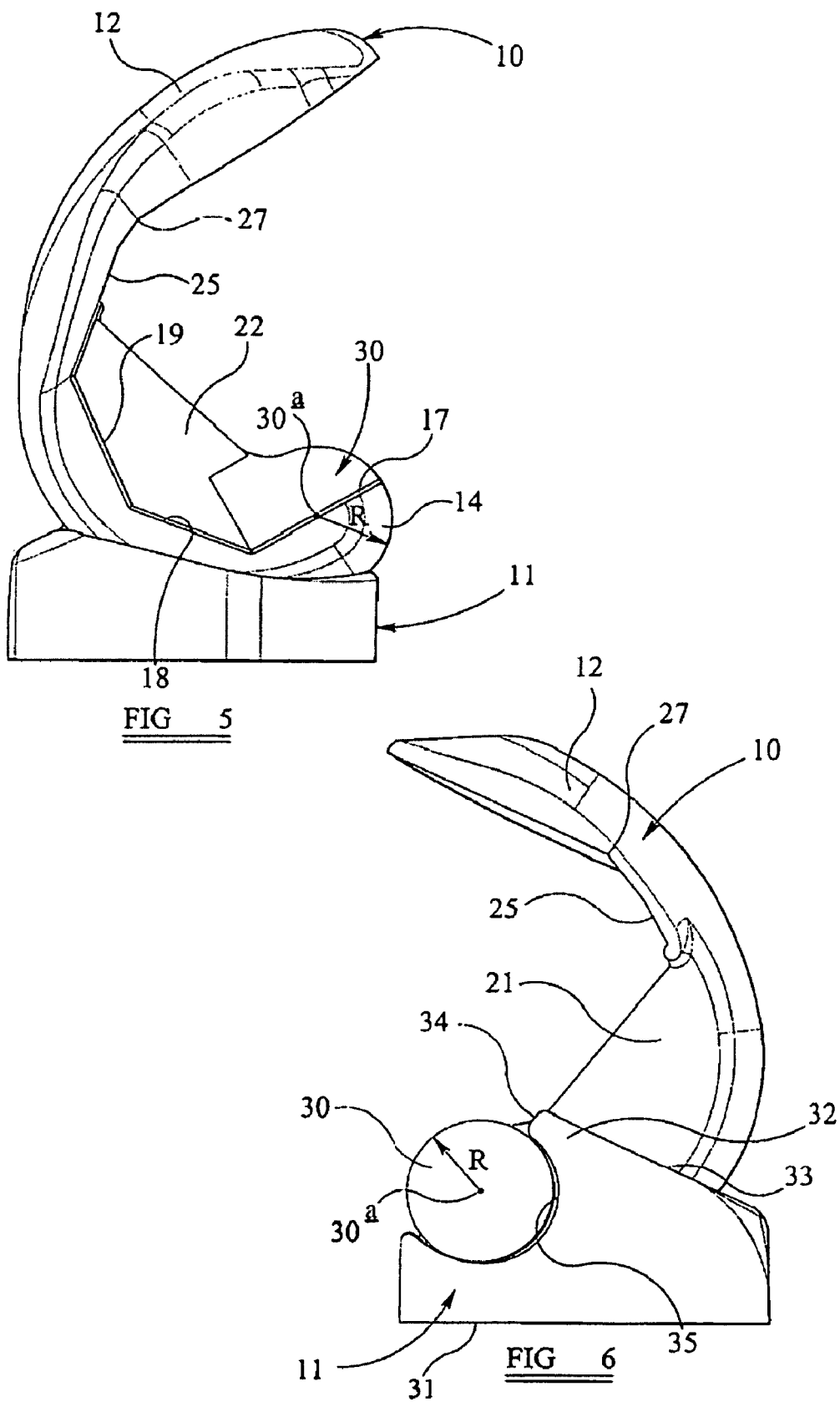

KNEE PROSTHESIS

CROSS REFERENCE TO RELATED APPLICATION

This application relates to and claims priority to corresponding Great Britain Patent Application No. 0510193.6, which was filed on May 19, 2005, and which is incorporated by reference herein.

BACKGROUND OF THE INVENTION

1. Field of the invention

This invention relates to a knee prosthesis for fitting to a patient as a replacement knee joint.

2. Related Art

Modern total knee replacement involves the resurfacing of the femoral condyles with a metallic component, roughly approximating to the shape of the anatomical femoral condyles, and resurfacing the tibial plateau with a polyethylene component having a metallic base plate. Conformity between the polyethylene of the tibial component and the metallic femoral component has historically been a troublesome area. Ideally the femoral component should be congruent with the top of the tibial component through all, or at least a significant proportion of the flexion of the knee. In knee replacements where the posterior cruciate ligament (PCL) is removed, various cam and post arrangements have been proposed to reproduce the stabilisation effect of the PCL, but these have not always proved effective over a normal range of knee flexion.

U.S. Pat. No. 4,298,992 discloses a knee prosthesis in which during flexion of the knee there is a camming action between a cam follower of the femoral prosthesis component and a cam surface of a post of the tibial prosthesis component. However it was found with this arrangement that with increasing flexion the contact point between the cam follower and the cam surface rises up the cam surface. This has two undesirable effects. Firstly this can lead to wear and deformation at the tip of the post, and secondly the cam follower can jump the post of the patient happens to achieve high flexion.

U.S. Pat. No. 6,123,729 also disclosures a knee prosthesis in which a cam surface engages an articular surface on a post during knee flexion. Whilst this represents an improvement over the prosthesis of U.S. Pat. No. 4,298,992, it suffers from there being a variable contact position of the cam surface on the post. This contact point moves from a position approximately half-way up the post at 90° of flexion, and then as flexion increases, firstly moves down the post and then up again at high flexion. A problem is that the main condyle-meniscal articulation with this prosthesis is incongruent, offering virtually no resistance to antero-posterior subluxation over the range of flexion 30° to 90°. Even at 60° of flexion, if the femur subluxes forward on the tibial component, then the cam surface/post contact point will be much higher up the post than for normal flexing.

SUMMARY OF THE INVENTION

The present invention seeks to obviate or at least minimise these disadvantages.

According to the invention there is provided a knee prosthesis comprising a femoral component for securement to the femur, a tibial component for securement to the tibia and a bearing component between the femoral and tibial components, the femoral component defining medial and lateral condyles and an open intercondylar area, the bearing component having respective surfaces shaped to match said condyles and engaging therewith both when the knee is extended and over a first range of flexion, and the femoral component defining at said intercondylar area one of a cam and follower and the bearing component defining the other of said cam and follower, the cam and follower engaging over a second range of flexion.

Preferably the cam defines a part-cylindrical surface, and desirably the follower has a matching at least part-cylindrical surface. Conveniently the follower surface is an interior concave surface of the bearing component and advantageously the cam is a convex cylindrical rod extending normally between the medial and lateral condyles of the femoral component. More preferably the rod is at the respective ends of the condyles of the femoral component. Desirably over said second range of flexion the central axis of the rod is coincident with the centre about which the radius defining the interior surface of the follower surface is struck. The centre of the rod is coincident with the centre of the radius on the posterior condyle of the femoral component. This prevents the contact/engagement between the cam and the follower surface moving up or down as the knee flexes over said second range of flexion.

Conveniently the congruent contact over the first range of flexion is from 0° to approximately 70°, and more conveniently the cam and follower engage over said second range of flexion from approximately 70° to approximately 160°, or whatever maximum flexion is with any given patient.

BRIEF DESCRIPTION OF THE DRAWINGS

The invention will now be described, by way of example, with reference to the accompanying drawings, in which:

FIGS. 4 and 5 are side views of the prosthesis shown at 0° flexion and 70° flexion respectively for a knee to which the prosthesis is fitted, in use, and FIG. 6 is a sectional side view corresponding to FIG. 5.

DETAILED DESCRIPTION OF THE INVENTION

Figure 1:
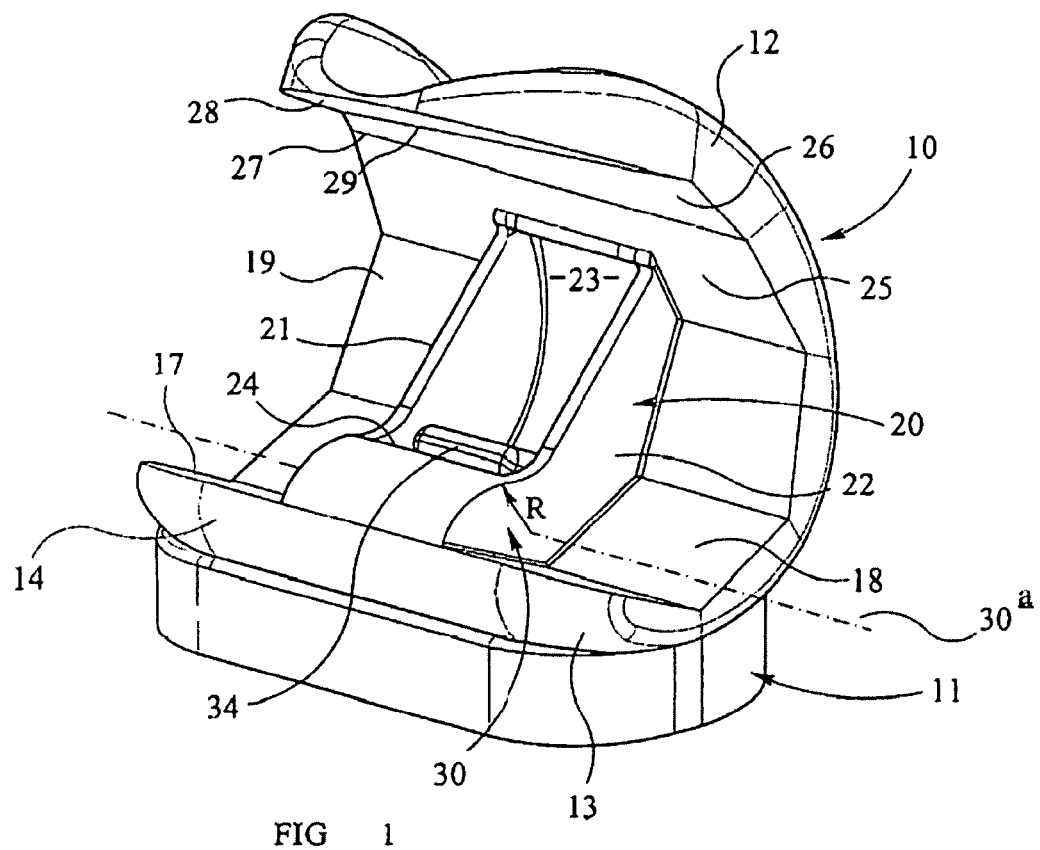
FIG. 1 is a perspective view of a replacement knee prosthesis of the invention in a position corresponding to a flexed knee.

As is well known, a knee prosthesis generally comprises a femoral component, a tibial component, and a meniscal or bearing component. Generally the femoral and tibial components are of metal with the bearing component being of plastics material such as polyethylene and fitting between the femoral and tibial components. In the accompanying drawings the tibial component is not shown, but it is to be understood that this would generally be of conventional form, such as in U.S. Pat. Nos. 5,387,240 and 5,658,342, having a flat upper surface in use, on which the flat lower surface of the bearing component engages, and a depending lower fixing stem. The femoral component shown in FIGS. 1 and 4 to 6 is indicated by the numeral 10 and the bearing component shown in FIGS. 1 to 6 is indicated by the numeral 11.

The knee replacement device shown in the drawings is of bicondylar form, with the femoral component 10 being a bicompartmental component. This is generally of known form defining a pair of spaced 'rounded' surfaces corresponding substantially to the condyles of the normal femur, i.e. the medial and lateral condyles thereof, the component 10 being a single one-piece construction.

Figure 2:
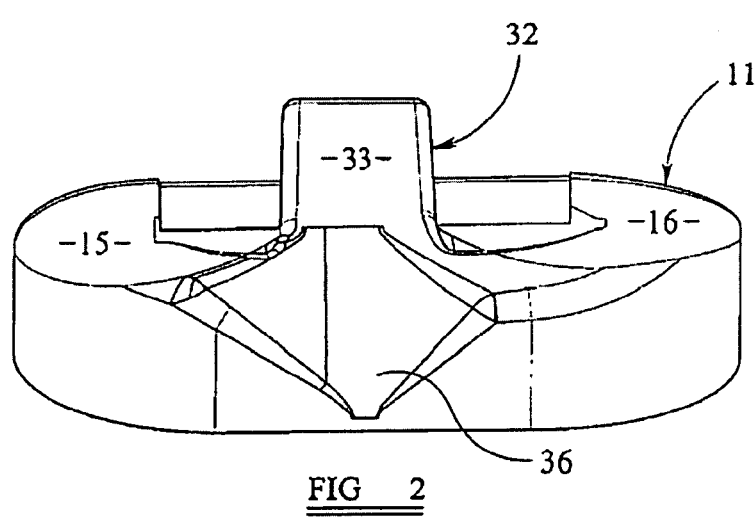
FIGS. 2 and 3 are a front view and a perspective view respectively of a bearing component of a replacement knee prosthesis of the invention.

The femoral component 10 is generally C-shaped, comprising a femoral flange 12 from the inner end of which extend spaced parallel lateral and medial condylar parts 13, 14 respectively, the respective undersurfaces of these condylar parts being part-spherical to mate, in use, in the normal way with the corresponding part-spherical surfaces 15, 16 of bearing component 11 shown in FIG. 2.

As can be seen from FIG. 1, the interior surface of each of the condylar parts 13, 14 is formed in three flat sections, a first flat section 17 of which is generally vertically upright, in use, when there is 0° of flexion of a knee to which the prosthesis is fitted, e.g. the person with the knee replacement is standing upright with a straight leg. Extending downwardly and inwardly at an obtuse angle from the first flat section 17 is a second flat section 18, and this terminates at a third flat section 19 which in the arrangement described where the first flat section is vertical, would be horizontal and be engaged, in use, by the lowermost resected part of the patient's femur, which will normally be a flat surface interrupted by the intercondylar or patella groove.

Interconnecting the two condylar parts 13, 14, is, in this embodiment, a box-like bridging part 20 which is made up of a pair of vertical parallel spaced flat side walls 21, 22 respectively at the respective inner edges of the condylar parts adjacent the intercondylar groove. Bridging part 20 is open at its top, i.e. between the walls 21, 22, defining a slot 23 which is closed at 24, near to the respective free ends of the condylar parts. Instead of the intercondylar box, there can be merely an open intercondylar area.

The intercondylar groove extends into and centrally divides a fourth flat section 25 of the internal surface of the femoral flange 12, the flat section 25 extending outwardly and upwardly from the third flat section of each condylar part by an obtuse angle. The side walls 21, 22 substantially terminate at this flat section 25. A fifth flat section 26 extends upwardly from the section 25 and slightly inwardly therefrom. The intercondylar groove terminates substantially at a junction line 27 between the fourth and fifth sections, but could terminate elsewhere, as required.

As described, the femoral component has its internal surface formed with a number of discrete flat sections with the junction lines between respective sections lying parallel to one another. This is the conventional shape of the interior surface of a femoral component, and is shown, for example, in British Patent Specification No. 2351236 and U.S. Patent Specification No. 6413279. With each of these prior art femoral components, the internal surface thereof is formed as five discrete flat sections with the first and fifth sections lying parallel to one another. With the femoral component 10 of FIG. 1, the first to third flat sections 17 to 19 are substantially shaped in the same way as with the prior art, with the third flat section 19 lying normal to the flat section 17. However instead of the inner surface of the femoral flange containing two flat sections, it will be noted that with the femoral component 10 of FIG. 1, the internal surface of the femoral flange 12 here comprises three separate flat sections, namely the fourth and fifth flat sections 25, 26 described above, and a sixth flat section 28 (FIG. 1) which extends to and defines the upper end of the femoral flange 12. However instead of this sixth flat section 28 being parallel to the first flat section 17 as is the case with the terminal end section of the femoral flange of the prior art femoral components, this sixth flat section is here angled outwardly at, for example, 10°, this being within the preferred range of 3° to 20°. Although the whole of the sixth flat section 28 is formed with this 'twisting' or 'divergence', it can be seen from FIG. 1 that this angle also effects the fifth flat section 26 to some degree, so that a junction line 29 (FIG. 1) between the sections 26 and 28 is not parallel to the junction line 27, but is angled due to the 'twisting' described. As can be seen from FIG. 1, the sixth flat section 28 extends inwardly (in the upwards direction) at an angle from the fifth flat section 26, and that as a result of the 'twisting' described, the flat internal surface of the sixth flat section 28 is angled relative to a plane which is normal to the third flat section 19, the plane also being normal to the length of the intercondylar groove. Accordingly unlike with the prior art femoral components, the flat internal surface at the extremity of the femoral flange is not parallel to the first flat section 17 at the extremity of the condylar part 13, 14.

The 'twisting' of the end part of the femoral flange forms the subject of my co-pending U.S. patent application Ser. No. 11/351,607, titled "Knee Prosthesis", filed concurrently herewith and incorporated herein by reference, to which reference should be made for further details.

Extending across the slot 23 in the bridging part 20, to close it at 24, and being connected at its respective opposite ends to respective facing sides of the condylar parts 13 and 14, is a cam in the form of a cylindrical rod 30. This rod 30 extends normally from said parallel facing sides of the condylar parts, and its axis 30a effectively lies parallel to the junction line 27.

The one-piece meniscal or bearing component 11 is of generally known shape, being of similar shape, in plan view, to the tibial component, not shown, with which the bearing component is associated. The bearing component has a planar undersurface 31 which serves, in use, as an articulatory bearing surface engaged with the upper flat planar surface of the tibial component. The upper surface of the bearing component provides bearing surfaces 15, 16 described above to match the exterior surfaces of the condylar parts 13, 14 respectively. Centrally of the component 11, but towards the slightly convex front peripheral side surface thereof is formed an upstanding peg 32, constituting a follower, with the opposite rear peripheral side surface of the bearing component being flat, with the peg 32 terminating short thereof.

Figure 3:
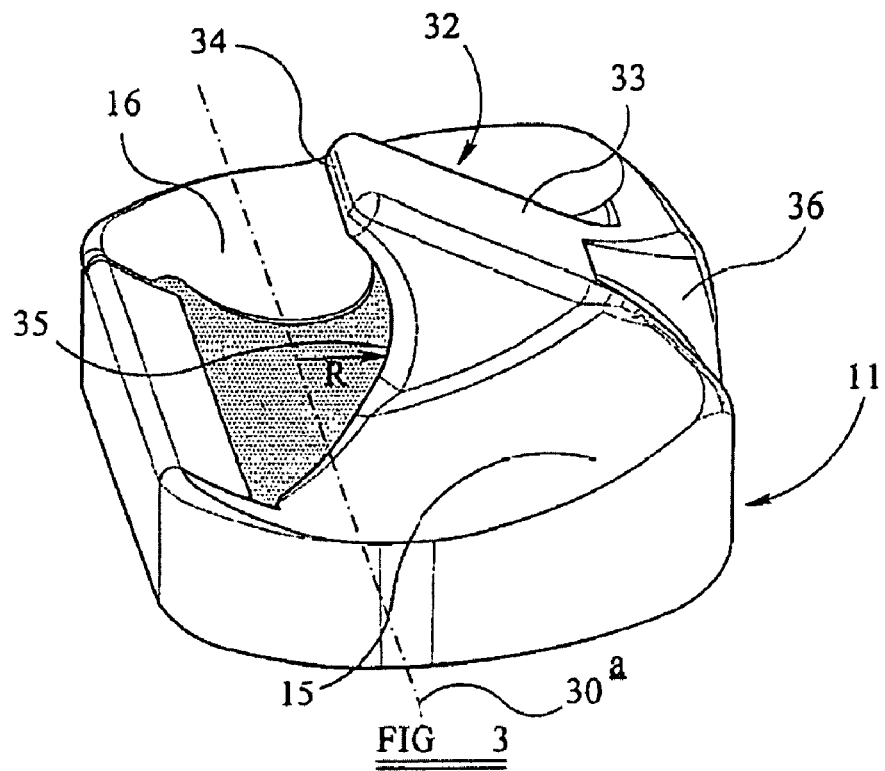

As can be seen from FIG. 3, the peg 32 has a body which rises with an upwardly angled flat top surface 33 from the front side surface to form an arcuate downwardly extending front nose part 34. Below this part 34 is a cam follower surface constituted by a recess 35 which is of part-cylindrical concave form to match the cylindrical external surface of the rod 30 so that, as will be described, rod 30 can engage in the recess 35 and follow the shape of the recess thereby allowing the femoral component 10 to move relative to the bearing component 11 during flexion of the knee. In the example shown in FIG. 6, the recess 35 extends through approximately 180° from the surface of the bearing component 11 between the bearing surfaces 15, 16 to the lower edge of the front part 34. However the angle through which the recess 35 extends can be varied as required, and the respective shapes of the inter-engaging parts of the cam (rod 30) and the follower (peg 32) can also be varied as required.

Figure 4:
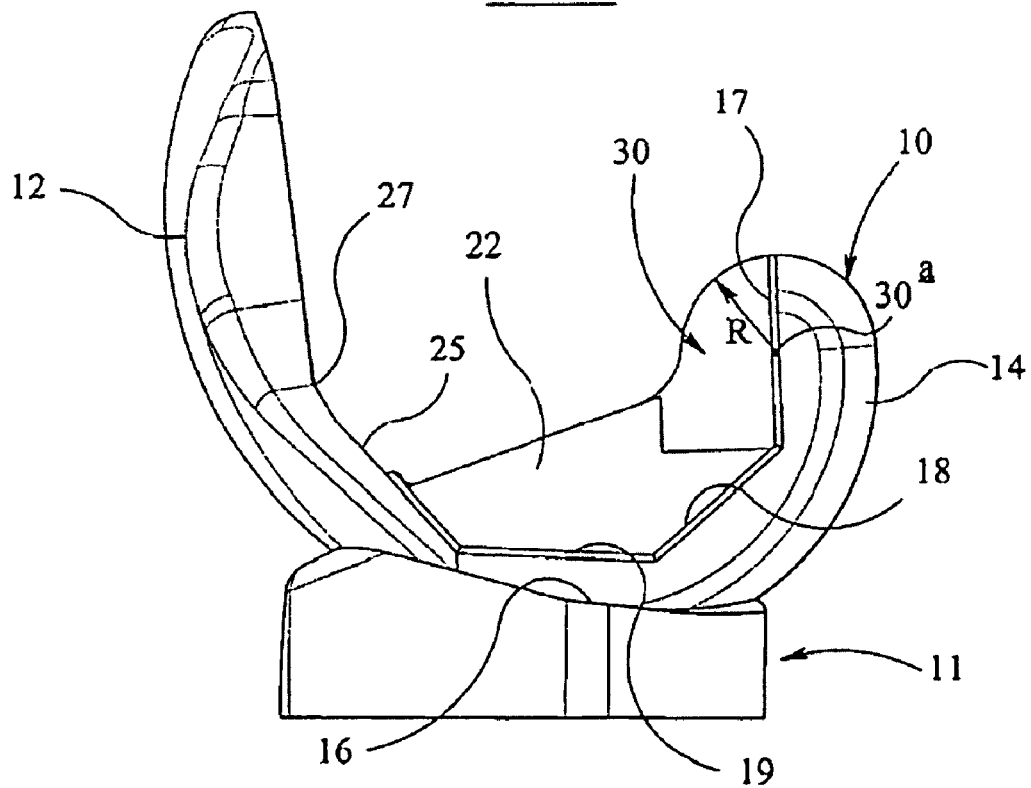

In the embodiment illustrated, it can be seen from FIGS. 3 and 4 that there is a lateralised recess 36 at the front side of the component 11 to accommodate a lateralised patella tendon.

As described in the introduction, one important requirement with a replacement knee is that there is congruency throughout as much of the flexion of the knee as is possible. With the arrangement shown in FIG. 4, where the femoral component 10 is fitted on the bearing component 11, and the knee is unflexed, it can be seen that the condylar parts 13 and 14, and in particular the exterior surface parts thereof corresponding to the third flat section 19, are in engagement with the corresponding bearing surfaces 15, 16, so that there is congruency at the start of the flexion of the knee. This congruency is maintained as flexion commences, with there being relative sliding movement between the femoral component 10 and the bearing component 11, as the respective exterior surfaces of the condylar parts 13, 14 slide over the corresponding bearing surfaces 15, 16 of the bearing component, with the knee flexing up to 90°. During this initial flexion, for example up to approximately 70°, the rod 30 remains clear of the inner surface of recess 35. This angle could be varied as required, and indeed in another embodiment there could be no engagement between the surface of recess 35 and the rod 30 until an angle of flexion of approximately 90° is reached. When the particular angle is reached, however, the rod 30 enters the recess 35 defined by the peg 32 and the matching of the external surface of the rod 30 with the internal surface of the recess 35 enables the relative sliding movement between the femoral component 10 and the bearing component 11 to continue, even though there could now be less engagement of the condylar parts 13, 14 with the bearing surfaces, 15, 16. However despite any such reduced engagement, contact is now maintained beyond 90°, for example up to approximately 160° or whatever maximum flexion is with any given patient, due to the rod 30 engaging against and following the form of the interior surface of the recess 35, thereby allowing continued flexion of the knee.

Accordingly with the disclosed embodiment femoro-meniscal articulation throughout the first range of flexion is congruent. This resists antero-posterior subluxtion of the femur on the meniscus, and the contact point of the peg and rod is always at the same position/area. In the embodiment disclosed, the centre of the rod is coincident with the centre of the small posterior radius R. Thus firstly there is congruent contract from 0 to 70. Then there is area contact between the rod and the peg up to about 160°. There is a large area of contact between the rod and the peg, as shown in FIG. 6, and moreover this contact area extends out into the meniscal bearing surfaces 15, 16, which are at respective opposite sides of the area shown shaded in FIG. 3. This is highly desirable as a calculated area contact of 300 to 600 mm² (depending on the diameter of the rod 30) should be consistent with low wear from low contact stress.

Unflexing of the knee is the reverse of the process described, with the rod 30 moving out of engagement with the peg 32 at approximately 70° of flexion, congruency taking place as the exterior surfaces respectively of the condylar parts 13, 14 slide relatively to the bearing surfaces 15, 16 of the bearing component until the knee is unflexed and the relative positions of the femoral and bearing components are again as shown in FIG. 4. FIGS. 1, 5 and 6 show the engagement of the rod 30 in the recess 35 at an angle of flexion of approximately 70°. The rod could, in an alternative embodiment, engage the cam at an angle of flexion greater or smaller than 70°, and the ranges of angular flexion for the two forms of engagements may overlap as described, or might not overlap.

It will be understood although the inventive feature of this application can be used independently of the inventive feature of my co-pending U.S. patent application Ser. No. 11/351,607, titled "Knee Prosthesis", filed concurrently herewith, it is advantageous if they are used together, thereby producing a greatly improved congruent knee prosthesis.

The invention claimed is:

1. A knee prosthesis comprising:
a femoral component for securement to the femur;
a tibial component for securement to the tibia; and
a bearing component between the femoral and tibial components,
the femoral component defining medial and lateral condyles having anterior and posterior portions and an open intercondylar area,
the bearing component having respective condylar bearing surfaces shaped to match said condyles, and
the femoral component defining at said intercondylar area one of a cam or follower and the bearing component defining the other of said cam or follower, the cam comprising a convex part-cylindrical surface and the follower comprising a matching concave part-cylindrical surface,
wherein the medial and lateral condyles are engaged with the bearing surfaces via a first congruent contact area both when the knee is extended and over a first range of flexion throughout which the cam and follower are disengaged,
a centre of a radius of curvature of each part-cylindrical surface of the cam and follower being coincident and also axially collinear with a centre of a radius of curvature of the posterior portions of the condyles of the femoral component, when the cam and follower part-cylindrical surfaces are engaged via a second-congruent contact area over a second range of flexion throughout which the cam and follower are engaged, and
wherein the second congruent contact area extends out into the respective condylar bearing surfaces.

2. A prosthesis as claimed in claim 1, wherein the follower is provided on the bearing component.

3. A prosthesis as claimed in claim 1, wherein the cam is a convex cylindrical rod extending normally between the medial and lateral condyles of the femoral component.

4. A prosthesis as claimed in claim 1, wherein the first range of flexion is from 0° to approximately 70°.

5. A prosthesis as claimed in claim 1, wherein the cam and follower engage over said second range of flexion from approximately 70° to approximately 160°.

6. A prosthesis as claimed in claim 1, wherein at a front side of the bearing component is a recess to accommodate, in use, a lateralised patella tendon.

7. A prosthesis as claimed in claim 1, wherein the lateral and medial condyles and the respective surfaces of the bearing component comprise part-spherical surfaces that are congruent over the first range of flexion.

8. A knee prosthesis comprising:
a femoral component for securement to the femur;
a tibial component for securement to the tibia; and
a bearing component between the femoral and tibial components,
the femoral component defining medial and lateral condyles having anterior and posterior portions and an open intercondylar area,
the bearing component having respective condylar bearing surfaces shaped to match said condyles, and
the femoral component defining at said intercondylar area one of a cam or follower and the bearing component defining the other of said cam or follower, wherein the cam defines a part-cylindrical surface, the follower has an at least part-cylindrical surface congruently matching said part-cylindrical cam surface, the follower surface is an interior concave surface of the bearing component, the cam is a convex cylindrical rod, and
wherein the medial and lateral condyles are engaged with the bearing surfaces via a first congruent contact area both when the knee is extended and over a first range of flexion throughout which the cam and follower are disengaged, a central axis of the rod being collinear with a centre of a radius defining the interior concave surface of the follower, and the central axis of the rod being collinear with a centre of a radius of curvature of the posterior portions of the condyles of the femoral component, when the cam and follower are engaged via a second congruent contact area over a second range of flexion throughout which the cam and follower are engaged, and wherein the second congruent contact area extends out into the respective condylar bearing surfaces.

9. A knee prosthesis comprising:

a femoral component for securement to the femur;

a tibial component for securement to the tibia; and a bearing component between the femoral and tibial components, the femoral component defining medial and lateral condyles and an open intercondylar area, the medial and lateral condyles each having posterior end portions, the bearing component having respective condylar bearing surfaces shaped to match said condyles, and the femoral component defining at said intercondylar area one of a cam or follower and the bearing component defining the other of said cam or follower, the cam comprising a convex part-cylindrical surface and the follower comprising a matching concave part-cylindrical surface, wherein the medial and lateral condyles are engaged with the bearing surfaces via a first congruent contact area over a first range of flexion, from full extension of the knee to a selected flexion angle, a center of a radius of curvature of each part-cylindrical surface of the cam and follower being coincident and also axially collinear with a centre of a radius of curvature of the posterior end portions of the condyles of the femoral component, when the cam and follower part-cylindrical surfaces are engaged via a second congruent contact area over a second range of flexion, from the selected flexion angle up to a maximum flexion of the knee.

10. A prosthesis as claimed in claim 9, wherein the second range of flexion extends up to an angle of approximately 160 degrees.

* * * * *